United States Patent
Mann et al.

(10) Patent No.: US 8,420,571 B2
(45) Date of Patent: Apr. 16, 2013

(54) SYNERGISTIC HERBICIDAL COMPOSITION CONTAINING FLUROXYPYR AND CYHALOFOP, METAMIFOP OR PROFOXYDIM

(75) Inventors: Richard K. Mann, Franklin, IN (US); Monte R. Weimer, Pittsboro, IN (US); Andrea Christine McVeigh-Nelson, Indianapolis, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 0 days.

(21) Appl. No.: 12/913,235

(22) Filed: Oct. 27, 2010

(65) Prior Publication Data

US 2011/0098181 A1    Apr. 28, 2011

Related U.S. Application Data

(60) Provisional application No. 61/255,685, filed on Oct. 28, 2009.

(51) Int. Cl.
*A01N 43/40*    (2006.01)

(52) U.S. Cl.
USPC .......................................................... 504/130

(58) Field of Classification Search .................. None
See application file for complete search history.

(56) References Cited

FOREIGN PATENT DOCUMENTS

| | | | |
|---|---|---|---|
| CN | 101 019 537 A | | 8/2007 |
| CN | 101 530 104 A | | 9/2009 |
| CN | 101530104 | * | 9/2009 |
| CN | 101 595 875 A | | 12/2009 |
| CN | 101 999 357 A | | 4/2011 |
| WO | WO 97/10710 A1 | | 3/1997 |
| WO | WO 03/047342 A1 | | 6/2003 |

OTHER PUBLICATIONS

U.S. Appl. No. 12/913,092; Synergistic Herbicidal Composition Containing Fluroxypyr and Penoxsulam, Halosulfuron-Methyl, Imazamox or Imazethapyr; filed Oct. 27, 2010; Inventors Richard K. Mann, Monte R. Weimer, Andrea C. McVeigh-Nelson, and Andrew Todd Ellis.

U.S. Appl. No. 12/913,152; Synergistic Herbicidal Composition Containing Fluroxypyr and Quinclorac; filed Oct. 27, 2010; Inventors Richard K. Mann and Andrea C. McVeigh-Nelson.

McCullough et al., "Fluroxypyr Compatibility with Fenoxaprop for Smooth Crabgrass and White Clover Control in Tall Fescue," Applied Turfgrass Science, XP 055022787 (2009).

McElroy et al., "Triclopyr Safens the Use of Fluazifop and Fenoxaprop on Zoysiagrass While Maintaining Bermudagrass Suppression," XP 055022791 (2006).

Doroh et al., "Triclopyr Enhances Metamifop and Clodinafop Control of Bermudagrass and Reduces Zoysiagrass Injury," 2009 Proceedings, Southern Weed Science Society, Orlando, Florida, 62:21, XP 002672253 (2009).

Lym et al, "Leafy spurge control with various picolinic acid herbicides," Leafy Spurge Symposium, Riverton, WY, Jul. 9-10, 1986, XP 055022790 (1986).

* cited by examiner

*Primary Examiner* — Alton Pryor

(74) *Attorney, Agent, or Firm* — Robert Chang

(57) ABSTRACT

An herbicidal composition containing (a) fluoroxypyr and (b) cyhalofop, metamifop or profoxydim provides synergistic control of selected weeds particularly on rice.

20 Claims, No Drawings

SYNERGISTIC HERBICIDAL COMPOSITION CONTAINING FLUROXYPYR AND CYHALOFOP, METAMIFOP OR PROFOXYDIM

FIELD OF THE INVENTION

This application claims the benefit of U.S. Provisional Application Ser. No. 61/255,685 filed on 28 Oct. 2009. This invention concerns a synergistic herbicidal composition containing (a) fluoroxypyr and (b) at least one herbicide selected from the group consisting of cyhalofop, metamifop or profoxydim for controlling weeds in crops, particularly in rice, but also other monocot crops such as corn, wheat, barley, oats, rye, sorghum, turf, pastures, grasslands, rangelands, fallowland and industrial vegetation management (IVM). These compositions provide improved post-emergence herbicidal weed control.

BACKGROUND OF THE INVENTION

The protection of crops from weeds and other vegetation which inhibit crop growth and adversely impact crop quality and yield is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462 "'synergism' [is] an interaction of two or more factors such that the effect when combined is greater than the predicted effect based on the response to each factor applied separately." The present invention is based on the discovery that fluoroxypyr, cyhalofop, metamifop and profoxydim, already known individually for their herbicidal efficacy, display a synergistic effect when applied in combination.

SUMMARY OF THE INVENTION

The present invention concerns a synergistic herbicidal mixture comprising an herbicidally effective amount of (a) fluoroxypyr and (b) an acetyl CoA carboxylase (ACCase) inhibitor herbicide. ACCase inhibitor herbicides include compounds from the classes of aryloxyphenoxypropionic acids and derivatives and cyclohexanediones. Particularly useful ACCase inhibitor herbicides include, but are not limited to, cyhalofop, metamifop and profoxydim. The compositions may also contain an agriculturally acceptable adjuvant and/or carrier.

The present invention also concerns herbicidal compositions for and methods of controlling the growth of undesirable vegetation, particularly in rice, but also other monocot crops such as corn, wheat, barley, oats, rye, sorghum, turf, pastures, grasslands, rangelands, fallowland and IVM, and the use of these synergistic compositions.

The species spectra of ACCase inhibitors like cyhalofop, metamifop and profoxydim, i.e., the weed species which the respective compounds control, are broad and highly complementary with that of fluoroxypyr. For example, it has been surprisingly found that a mixture of cyhalofop and fluoroxypyr exhibits a synergistic action in the control of barnyardgrass (*Echinochloa crus-galli*; ECHCG), tighthead sprangletop (*Leptochloa panicoides* (L.); LEFPA), Chinese sprangletop (*Leptochloa chinensis* (L.); LEFCH), broadleaf signalgrass (*Brachiaria platyphylla* (GRISEB.) NASH; BRAPP), winklegrass (*Ischaemum rugosum* SALISB.; ISCRU), and giant foxtail (*Setaria faberi*; SETFA) at application rates equal to or lower than the rates of the individual compounds. Similarly, it has been surprisingly found that a mixture of metamifop and fluoroxypyr exhibits a synergistic action in the control of barnyardgrass (*Echinochloa crus-galli*; ECHCG), Chinese sprangletop (*Leptochloa chinensis* (L.); LEFCH), and broadleaf signalgrass (*Brachiaria platyphylla* (GRISEB.) NASH; BRAPP) at application rates equal to or lower than the rates of the individual compounds. In addition, it has been surprisingly found that a mixture of profoxydim and fluoroxypyr exhibits a synergistic action in the control of barnyardgrass (*Echinochloa crus-galli*; ECHCG) and Chinese sprangletop (*Leptochloa chinensis* (L.); LEFCH) at application rates equal to or lower than the rates of the individual compounds.

DETAILED DESCRIPTION OF THE INVENTION

Cyhalofop is the common name for (2R)-2-[4-(4-cyano-2-fluorophenoxy)phenoxy]-propanoic acid. Its herbicidal activity is described in *The Pesticide Manual*, Fourteenth Edition, 2006. Cyhalofop provides post-emergence control of grass weeds in rice. It can be used as the acid itself or as an agriculturally acceptable salt or ester. Use as an ester is preferred, with the butyl ester being most preferred.

Metamifop is the common name for (2R)-2-[4-[(6-chloro-2-benzoxazolyl)oxy]-phenoxy]-N-(2-fluorophenyl)-N-methylpropanamide. Its herbicidal activity is described in *The Pesticide Manual*, Fourteenth Edition, 2006. Metamifop provides post-emergence control of grass weeds in rice and turf.

Profoxydim is the common name for 2-[1-[[2-(4-chlorophenoxy)propoxy]imino]-butyl]-3-hydroxy-5-(tetrahydro-2H-thiopyran-3-yl)-2-cyclohexen-1-one. Its herbicidal activity is described in *The Pesticide Manual*, Fourteenth Edition, 2006. Profoxydim provides post-emergence control of grass weeds in rice.

Fluoroxypyr is the common name for [(4-amino-3,5-dichloro-6-fluoro-2-pyridinyl)oxy]acetic acid. Its herbicidal activity is described in *The Pesticide Manual*, Fourteenth Edition, 2006. Fluoroxypyr controls a wide range of economically important broadleaf weeds. It can be used as the acid itself or as an agriculturally acceptable salt or ester. Use as an ester is preferred, with the meptyl ester being most preferred.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of fluoroxypyr (acid equivalent) to cyhalofop (acid equivalent) at which the herbicidal effect is synergistic lies within the range of between about 1:12 and about 16:1. The weight ratio of fluoroxypyr (acid equivalent) to metamifop and profoxydim (active ingredient) at which the herbicidal effect is synergistic lies within the range of between about 1:10 and about 75:1.

The rate at which the synergistic composition is applied will depend upon the particular type of weed to be controlled, the degree of control required, and the timing and method of application. In general, the composition of the invention can be applied at an application rate of cyhalofop between about 32 g ae/ha and about 430 g ae/ha and an application rate of fluoroxypyr between about 35 g ae/ha and about 560 g ae/ha. In general, the composition of the invention can be applied at an application rate of metamifop or profoxydim between about 7.5 g ai/ha and about 350 g ai/ha and an application rate of fluoroxypyr between about 35 g ae/ha and about 560 g ae/ha The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 2,4-D, acetochlor, acifluorfen, aclonifen, AE0172747, alachlor, amidosulfuron, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cyclosydim, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+isoxadifen-ethyl, fentrazamide, flazasulfuron, florasulam, fluazifop, fluazifop-P-butyl, flucetosulfuron (LGC-42153), flufenacet, flufenpyr-ethyl, flumetsulam, flumiclorac-pentyl, flumioxazin, fluometuron, flupyrsulfuron, fomesafen, foramsulfuron, flumiclorac, glufosinate, glufosinate-ammonium, glyphosate, halosulfuron, haloxyfop-methyl, haloxyfop-R, imazamethabenz, imazamox, imazapic, imazapyr, imazaquin, imazethapyr, imazosulfuron, indanofan, indaziflam, iodosulfuron, ioxynil, ipfencarbazone (HOK-201), IR 5790, isoproturon, isoxaben, isoxaflutole, KUH-021, lactofen, linuron, MCPA, MCPA ester & amine, mecoprop-P, mefenacet, mesosulfuron, mesotrione, metazosulfuron (NC-620), metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, penoxsulam, pentoxazone, pethoxamid, picloram, picolinafen, piperophos, pretilachlor, primisulfuron, propachlor, propanil, propyrisulfuron (TH-547), propyzamide, prosulfocarb, prosulfuron, pyraclonil, pyrazogyl, pyrazosulfuron, pyribenzoxim (LGC-40863), pyriftalid, pyriminobac-methyl, pyrimisulfan (KUH-021), pyroxsulam, pyroxasulfone (KIH-485), quinclorac, quizalofop-ethyl-D, quizalofop-P-ethyl, S-3252, sethoxydim, simazine, SL-0401, SL-0402, S-metolachlor, sulcotrione, sulfentrazone, sulfosate, tebuthiuron, tefuryltrione (AVH-301), terbacil, thiazopyr, thiobencarb, triclopyr, trifluralin and tritosulfuron.

The synergistic composition of the present invention can, further, be used in conjunction with glyphosate, glufosinate, dicamba, imidazolinones, sulfonylureas or 2,4-D on glyphosate-tolerant, glufosinate-tolerant, dicamba-tolerant, imidazolinone-tolerant, sulfonylurea-tolerant or 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity. Cloquintocet (mexyl) is a particularly preferred safener for the synergistic compositions of the present invention, specifically antagonizing any harmful effect of the synergistic compositions on rice and cereals.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO) and PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers, latex and the like. Water is generally the carrier of choice for the dilution of concentrates.

Suitable solid carriers include KCl, talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, various forms of cellulose, corn cob grit and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters; vegetable oils such as soybean oil, rapeseed oil, olive oil, castor oil, sunflower seed oil, coconut oil, corn oil, cottonseed oil, canola oil, linseed oil, palm oil, peanut oil, safflower oil, sesame oil, tung oil and the like; and esters of the above vegetable oils.

Other additives commonly used in agricultural compositions include compatibility agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 10 to 90 weight percent. Such compositions are typically diluted with an inert carrier, such as water, before application, or applied as a dry or liquid formulation directly into flooded rice fields. The diluted compositions usually applied to weeds or the locus of weeds generally contain 0.0001 to 10 weight percent active ingredient and preferably contain 0.001 to 5.0 weight percent.

The present compositions can be applied to weeds or their locus by the use of conventional hand, ground or aerial dusters, sprayers, and granule applicators, by addition to irrigation or paddy water, and by other conventional means known to those skilled in the art.

The following examples illustrate the present invention.

EXAMPLES

Evaluation of Postemergence Herbicidal Activity of Mixtures in the Greenhouse

Seeds of the desired test plant species were planted in 80% mineral soil/20% grit planting mixture, which typically has a pH of 7.2 and an organic matter content of about 2.9 percent, in plastic pots with a surface area of 128 square centimeters ($cm^2$). The growing medium was steam sterilized. The plants were grown for 7-19 days in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were treated with postemergence foliar applications when they reached the third to fourth true leaf stage. All treatments were applied using a randomized complete block trial design, with 4 replications per treatment.

Evaluation of Postemergence Herbicidal Activity of Mixtures in the Greenhouse

Treatments consisted of the compounds as listed in Tables 1, 2, 4 and 5 with each compound applied alone and in combination. Formulated amounts of cyhalofop-butyl, metamifop, profoxydim and fluoroxypyr-meptyl ester, were placed in 60 milliliter (mL) glass vials and dissolved in a volume of 60 mL of a water solution containing Agri-dex crop oil concentrate in a 1% volume per volume (v/v) ratio. Compound requirements are based upon a 12 mL application volume at a rate of 187 liters per hectare (L/ha). Spray solutions of the mixtures were prepared by adding the stock solutions to the appropriate amount of dilution solution to form 12 mL spray solution with active ingredients in single and two way combinations. Formulated compounds were applied to the plant material with an overhead Mandel track sprayer equipped with 8002E nozzles calibrated to deliver 187 L/ha at a spray height of 18 inches (43 centimeters (cm)) above average plant canopy.

The treated plants and control plants were placed in a greenhouse as described above and watered by sub-irrigation to prevent wash-off of the test compounds. Treatments were rated at 14 to 21 days after application as compared to the untreated control plants. Percent visual weed control was scored on a scale of 0 to 100 percent where 0 corresponds to no injury and 100 corresponds to complete kill.

Evaluation of Postemergence Herbicidal Activity of Mixtures in the Field

Field trials were conducted in drill-seeded rice using standard herbicide small plot research methodology. Plots were typically 3×10 meters (m, width×length) in size with 4 replicates per treatment. The rice crop was grown using normal cultural practices for fertilization, seeding, watering, flooding and maintenance to ensure good growth of the crop and the weeds.

All treatments in the field trials were applied using a carbon dioxide ($CO_2$) backpack sprayer calibrated to apply 187 L/ha spray volume. Commercially available products of cyhalofop-butyl and fluoroxypyr-meptyl were mixed in water at appropriately formulated product rates to achieve the desired rates based on a unit area of application (hectare) to achieve the desired application rates as shown. Treatments were rated at 29 to 36 days after application (DAA) as compared to the untreated control plants. Percent visual weed control was scored on a scale of 0 to 100 percent where 0 corresponds to no injury and 100 corresponds to complete kill.

Table 3 demonstrates the herbicidal synergistic efficacy of cyhalofop-butyl+fluoroxypyr-meptyl tank mixes on weed control in the field. All treatment results, both for the single product and mixtures, are an average of 4 replicates and the tank mix interactions are significant at the P>0.05 level using Tukey's T-test.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

TABLE 1

Synergistic Activity of Herbicidal Compositions on Key Grass Weeds in Rice in the Greenhouse at 14 days after application (DAA).

| Application Rate (g ae/ha) | | % Control | | | | | |
|---|---|---|---|---|---|---|---|
| | | ECHCG | | BRAPP | | ISCRU | |
| Cyhalofop | Fluroxypyr | Ob | Ex | Ob | Ex | Ob | Ex |
| 63 | 0 | 55 | — | — | — | — | — |
| 0 | 70 | 14 | — | — | — | — | — |
| 63 | 70 | 96 | 61 | — | — | — | — |
| 63 | 0 | 55 | — | — | — | — | — |
| 0 | 140 | 9 | — | — | — | — | — |
| 63 | 140 | 88 | 60 | — | — | — | — |
| 63 | 0 | 55 | — | — | — | — | — |
| 0 | 280 | 8 | — | — | — | — | — |
| 63 | 280 | 91 | 59 | — | — | — | — |
| 126 | 0 | 73 | — | — | — | — | — |
| 0 | 70 | 14 | — | — | — | — | — |
| 126 | 70 | 99 | 77 | — | — | — | — |
| 126 | 0 | 73 | — | — | — | 15 | — |
| 0 | 140 | 9 | — | — | — | 15 | — |
| 126 | 140 | 97 | 75 | — | — | 44 | 28 |
| 126 | 0 | 73 | — | — | — | — | — |
| 0 | 280 | 8 | — | — | — | — | — |
| 126 | 280 | 98 | 75 | — | — | — | — |
| 253 | 0 | — | — | 77 | — | — | — |
| 0 | 70 | — | — | 22 | — | — | — |
| 253 | 70 | — | — | 92 | 82 | — | — |
| 253 | 0 | — | — | 77 | — | — | — |
| 0 | 140 | — | — | 16 | — | — | — |
| 253 | 140 | — | — | 89 | 81 | — | — |

TABLE 2

Synergistic Activity of Herbicidal Compositions on Key Grass Weeds in Rice in the Greenhouse at 21 DAA.

| Application Rate (g ae/ha) | | % Control | | | |
|---|---|---|---|---|---|
| | | LEFCH | | SETFA | |
| Cyhalofop | Fluroxypyr | Ob | Ex | Ob | Ex |
| 63 | 0 | 67 | — | — | — |
| 0 | 70 | 28 | — | — | — |
| 63 | 70 | 87 | 77 | — | — |
| 63 | 0 | 67 | — | 82 | — |
| 0 | 140 | 5 | — | 50 | — |
| 63 | 140 | 94 | 69 | 97 | 91 |

TABLE 3

Synergistic Activity of Herbicidal Compositions on Key Grass Weeds in Rice in the Field at 29-36 DAA.

| Application Rate (g ae/ha) | | % Control | | | |
|---|---|---|---|---|---|
| | | LEFPA | | ECHCG | |
| Cyhalofop | Fluroxypyr | Ob | Ex | Ob | Ex |
| 262 | 0 | 33 | — | — | — |
| 0 | 190 | 0 | — | — | — |
| 262 | 190 | 74 | 33 | — | — |
| 262 | 0 | 33 | — | — | — |
| 0 | 290 | 3 | — | — | — |
| 262 | 290 | 75 | 34 | — | — |
| 262 | 0 | 33 | — | 67 | — |
| 0 | 580 | 0 | — | 0 | — |
| 262 | 580 | 78 | 33 | 77 | 67 |

TABLE 4

Synergistic Activity of Herbicidal Compositions of Fluroxypyr-meptyl + Metamifop on Key Grass Weeds in Rice in the Greenhouse at 21 DAA.

| Application Rate | | % Control | | | | | |
|---|---|---|---|---|---|---|---|
| Metamifop (g ai/ha) | Fluroxypyr (g ae/ha) | ECHCG Ob | Ex | BRAPP Ob | Ex | LEFCH Ob | Ex |
| 7.5 | 0 | 5 | — | 25 | — | — | — |
| 0 | 50 | 0 | — | 5 | — | — | — |
| 7.5 | 50 | 22 | 5 | 58 | 29 | — | — |
| 15 | 0 | 33 | — | 54 | — | — | — |
| 0 | 50 | 0 | — | 5 | — | — | — |
| 15 | 50 | 70 | 33 | 75 | 56 | — | — |
| 30 | 0 | 74 | — | — | — | 88 | — |
| 0 | 50 | 0 | — | — | — | 6 | — |
| 30 | 50 | 86 | 74 | — | — | 100 | 89 |
| 7.5 | 0 | — | — | 25 | — | — | — |
| 0 | 100 | — | — | 1 | — | — | — |
| 7.5 | 100 | — | — | 55 | 26 | — | — |
| 15 | 0 | 33 | — | 54 | — | — | — |
| 0 | 100 | 11 | — | 1 | — | — | — |
| 15 | 100 | 75 | 40 | 76 | 54 | — | — |
| 30 | 0 | 74 | — | — | — | — | — |
| 0 | 100 | 11 | — | — | — | — | — |
| 30 | 100 | 95 | 76 | — | — | — | — |
| 7.5 | 0 | — | — | 25 | — | 23 | — |
| 0 | 200 | — | — | 5 | — | 41 | — |
| 7.5 | 200 | — | — | 60 | 28 | 74 | 54 |
| 15 | 0 | — | — | 54 | — | — | — |
| 0 | 200 | — | — | 5 | — | — | — |
| 15 | 200 | — | — | 65 | 55 | — | — |
| 30 | 0 | 74 | — | — | — | — | — |
| 0 | 200 | 6 | — | — | — | — | — |
| 30 | 200 | 90 | 75 | — | — | — | — |

TABLE 5

Synergistic Activity of Herbicidal Compositions of Fluroxypyr-meptyl + Profoxydim on Key Grass Weeds in Rice in the Greenhouse at 21 DAA.

| Application Rate | | % Control | | | |
|---|---|---|---|---|---|
| Profoxydim (g ai/ha) | Fluroxypyr (g ae/ha) | ECHCG Ob | ECHCG Ex | LEFCH Ob | LEFCH Ex |
| 25 | 0 | 54 | — | — | — |
| 0 | 50 | 0 | — | — | — |
| 25 | 50 | 98 | 54 | — | — |
| 25 | 0 | 54 | — | 61 | — |
| 0 | 100 | 0 | — | 41 | — |
| 25 | 100 | 91 | 54 | 86 | 77 |
| 25 | 0 | 54 | — | 61 | — |
| 0 | 200 | 5 | — | 48 | — |
| 25 | 200 | 94 | 56 | 99 | 80 |
| 50 | 0 | — | — | 78 | — |
| 0 | 200 | — | — | 49 | — |
| 50 | 200 | — | — | 100 | 89 |

BRAPP = *Brachiaria platyphylla*, broadleaf signalgrass
ECHCG = *Echinochloa crus-galli*, barnyardgrass
ISCRU = *Ischaemum rugosum*, winklegrass
LEFCH = *Leptochloa chinensis*, Chinese sprangletop
LEFPA = *Leptochloa panicoides*, tighthead sprangletop
SETFA = *Setaria faberi*, giant foxtail
Ob = observed value (% control)
Ex = expected, calculated value using Colby Analysis (% control)
DAA = days after application
g ae/ha = grams of acid equivalent per hectare
g ai/ha = grams of active ingredient per hectare

What is claimed is:

1. A synergistic herbicidal mixture comprising an herbicidally effective amount of (a) fluroxypyr, or an agriculturally acceptable salt or ester thereof, and (b) an ACCase inhibitor herbicide, wherein the ACCase inhibitor herbicide is cyhalofop, or an agriculturally acceptable salt or ester thereof, metamifop, or profoxydim.

2. The mixture of claim 1, comprising the meptyl ester of fluroxypyr.

3. The mixture of claim 1 in which the ACCase inhibitor herbicide is cyhalofop, or an agriculturally acceptable salt or ester thereof, or metamifop.

4. The mixture of claim 3 in which the ACCase inhibitor herbicide is the butyl ester of cyhalofop.

5. The mixture of claim 1 in which the ACCase inhibitor is profoxydim.

6. The mixture of claim 1 in which the weight ratio of fluroxypyr (acid equivalent) to cyhalofop (acid equivalent) is between about 1:12 and about 16:1.

7. The mixture of claim 1 in which the weight ratio of fluroxypyr (acid equivalent) to metamifop or profoxydim (active ingredient) is between about 1:10 and about 75:1.

8. An herbicidal composition comprising an herbicidally effective amount of the herbicidal mixture of claim 1 and an agriculturally acceptable adjuvant and/or carrier.

9. A method of controlling undesirable vegetation which comprises contacting the vegetation, locus of the vegetation, or water where the undesirable vegetation is to be controlled an herbicidally effective amount of the herbicidal mixture of claim 1.

10. The method of claim 9, wherein the undesirable vegetation is controlled in rice.

11. The method of claim 10, wherein the synergistic herbicidal mixture of claim 1 is applied at an application rate of cyhalofop between about 32 g ae/ha and about 430 g ae/ha and an application rate of fluroxypyr between about 35 g ae/ha and about 560 g ae/ha.

12. The method of claim 9, wherein the undesirable vegetation is barnyardgrass, tighthead sprangletop, Chinese sprangletop, broadleaf signalgrass, winklegrass, or giant foxtail.

13. The mixture of claim 6, in which the weight ratio of fluroxypyr (acid equivalent) to cyhalofop (acid equivalent) ranges from 1:3.6 to 4.4:1.

14. The mixture of claim 7, in which the weight ratio of fluroxypyr (acid equivalent) to metamifop (active ingredient) ranges from 1.7:1 to 27:1.

15. The mixture of claim 7, in which the weight ratio of fluroxypyr (acid equivalent) to profoxydim (active ingredient) ranges from 2:1 to 8:1.

16. The method of claim 10, wherein the synergistic herbicidal mixture of claim 1 is applied at an application rate of metamifop or profoxydim between about 7.5 g ai/ha and about 350 g ai/ha and an application rate of fluroxypyr between about 35 g ae/ha and about 560 g ae/ha.

17. A method of controlling undesirable vegetation which comprises contacting the vegetation, locus of the vegetation, or water where the undesirable vegetation is to be controlled with a synergistically effective amount of (a) fluroxypyr, or an agriculturally acceptable salt or ester thereof, and (b) an ACCase inhibitor herbicide, wherein the ACCase inhibitor herbicide is cyhalofop, or an agriculturally acceptable salt or ester thereof, metamifop, or profoxydim.

18. The method of claim 17, which comprises contacting the vegetation, locus of the vegetation, or water where the undesirable vegetation is to be controlled with asynergistically effective amount of (a) the meptyl ester of fluroxypyr, and (b) the butyl ester of cyhalofop.

19. The method of claim 17, which comprises contacting the vegetation, locus of the vegetation, or water where the undesirable vegetation is to be controlled with a synergistically effective amount of (a) the meptyl ester of fluroxypyr, and (b) metamifop.

20. The method of claim 17, which comprises contacting the vegetation, locus of the vegetation, or water where the undesirable vegetation is to be controlled with a synergistically effective amount of (a) the meptyl ester of fluroxypyr, and (b) profoxydim.

* * * * *